United States Patent [19]

D'Angelo et al.

[11] 3,991,109

[45] Nov. 9, 1976

[54] DIACYL PEROXY COMPOUNDS

[75] Inventors: Antonio Joseph D'Angelo; Orville Leonard Mageli, both of Buffalo, N.Y.

[73] Assignee: Pennwalt Corporation, Philadelphia, Pa.

[22] Filed: Jan. 12, 1976

[21] Appl. No.: 648,216

Related U.S. Application Data

[60] Division of Ser. No. 493,369, July 31, 1974, Pat. No. 3,952,041, which is a continuation of Ser. No. 211,092, Dec. 22, 1971, abandoned, which is a division of Ser. No. 727,323, May 7, 1968, Pat. No. 3,671,651.

[52] U.S. Cl. .......................... 260/544 Y; 260/2 EP; 260/13; 260/75 T; 260/463; 260/453 R; 260/475 P; 260/476 C; 260/485 C; 260/485 P; 260/544 L; 260/544 B; 260/544 R; 260/545 R; 260/546; 260/879; 260/880 R; 260/881; 260/884; 260/885; 260/886; 260/934; 526/7; 526/335; 526/340; 526/346; 526/347

[51] Int. Cl.$^2$ .................. C07C 59/32; C07C 61/36; C07C 65/20

[58] Field of Search ......... 260/544 L, 544 B, 544 P, 260/544 Y

[56] References Cited
UNITED STATES PATENTS

| | | |
|---|---|---|
| 2,978,495 | 4/1961 | Frankel et al. .................. 260/544 Y |
| 3,165,546 | 1/1965 | Merrill ............................ 260/544 X |
| 3,288,855 | 11/1966 | Schisla et al. ................... 260/544 Y |
| 3,632,630 | 1/1972 | Chao et al. ...................... 260/544 Y |
| 3,646,108 | 2/1972 | Jones et al. ..................... 260/544 B |

*Primary Examiner*—Norman Morganstern

[57] ABSTRACT

I. A novel class of compounds $X_n-R_p-Y_m$ where R is a 2–4 valence aliphatic, cycloaliphatic or aromatic radical, X is an acylating function; Y is a peroxy containing group and n and m are each equal to 1–2 and p is at least 1.

II. A novel class of polymers $[A_n-(R-D_n)_n]_v-P_w-Z$ where A is a peroxy containing group; R is a 2–4 valence aliphatic, cycloaliphatic or aromatic radical, P is a polyvalent polymeric residue; D is a carbonyl containing connecting group; Z is H, OH, $NH_2$, $NHR_2$, SH or $R_2O$ group; v and w are each equal to 1-100; and n is equal to 1–2.

III. Polymers II are useful with vinyl monomers in the formation of block and graft polymers.

IV. Peroxides having an acylating function are prepared by reacting at 0°–80° C an organic peroxide having an hydroxyl or carboxyl group with a defined acylating reactant.

V. Peroxides having at least one acylating function are prepared by peroxidizing a compound having at least two acylating functions as the only peroxidizable substituents.

2 Claims, No Drawings

DIACYL PEROXY COMPOUNDS

This is a division of application Ser. No. 493,369, filed July 31, 1974, now U.S. Pat. No. 3,952,041 which in turn is a continuation of application Ser. No. 211,092, filed Dec. 22, 1971, now abandoned, which in turn is a division of application Ser. No. 727,323, filed May 7, 1968, now U.S. Pat. No. 3,671,651.

BACKGROUND OF THE INVENTION

This invention relates to novel compounds having both a poroxy group and an acylating function and to polymers having at least one peroxy group. Also the invention relates to methods for preparing compounds having both a peroxy group and an acylating function. Also the invention relates to a method of making block and graft polymers from vinyl-type monomers.

THE PRIOR ART

Aliphatic t-alkyl peroxy chloroformate and di-t-alkyl and aralkyl peroxides containing acylating groups are known. A. G. Davies et al, J. Chem. Soc. (1953) p 1808 et seq. prepared aliphatic t-alkyl peroxy chloroformates, such as,

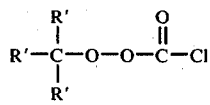

t-alkyl peroxy chloroformate by reacting t-alkyl hydroperoxide with phosgene. The following derivatives were also prepared by reaction of the

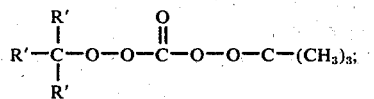 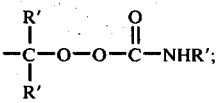 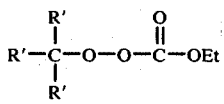

chloroformate with t-butyl hydroperoxide, amines and alcohols. (This type of peroxy compounds containing acylating groups do not fall within the scope of our invention because the peroxy group is not separated from the chloroformyl group and actually is a part of it.)

The di-t-alkyl peroxides containing acylating groups represented by the following structures

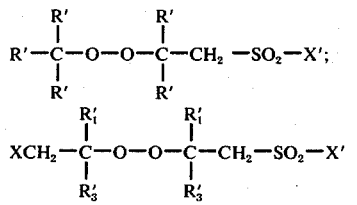

where $R_1'$ and $R'$ are lower alkyl radicals, $R_3'$ is lower alkyl or aromatic radical, $X'$ is either Cl or Br were prepared in U.S. Pat. No. 2,519,403. Derivatives prepared from the above structures were obtained by replacement of the halogen in $-SO_2-X'$ group with hydroperoxides, alcohols, ammonia, primary and secondary amines in U.S. Pat. No. 2,542,578. (These compounds do not fall within the scope of this invention because the connecting link is $-SO_2-$ rather than

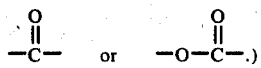

Di-t-aralkyl peroxides containing as acylating groups

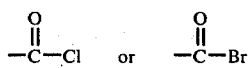

represented by the following structure:

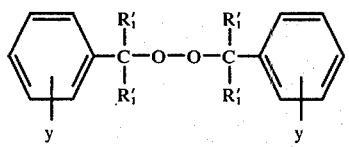

where $R_1'$ is the same or different alkyl radical and $y$ is

or

group were prepared in U.S. Pat. No. 3,165,546.

The above peroxy compounds do not come within this invention. They have many disadvantages:

1. They are too thermally stable to be useful for vinyl polymerization.
2. When reacted with polymers containing more than two functional groups, the polymer obtained is a crosslinked one which is not useful for block and graft work due to the inherent insolubility of crosslinked polymer in most organic solvents.
3. They can only be used in condensation reaction to prepare polyesters, polyamides, etc. and even in applications such as these, the resultant polymer, in order to be useful for block and graft work, an outside source of radiation has to be used in order to decompose the peroxide.
4. They do not offer a wide range of operating temperature which is so important when working with the preparation of graft and block copolymers from different vinyl monomers.

With peroxidic materials one of ordinary skill in the art would not use the reaction conditions necessary to convert any peroxy compound containing carboxylic or alcohol groups to the desired corresponding acid halide, anhydride and chloroformate. He would expect decomposition of the peroxide to take place especially with peroxides of the diperketals, perester, and diacyl type.

SUMMARY OF THE INVENTION

I. A class of compounds having at least one peroxy group and at least one acylating function defined by the following general formula:

$$X_n-R_p-Y_m$$

where:
1. R is an aliphatic, cycloaliphatic or aromatic radical having 2–4 valences available for X and Y;
2. $p$ is an integer equal to at least 1;
3. X is selected from the class consisting of

4. B is Cl- or Br-;
5. Y is selected from the class consisting of

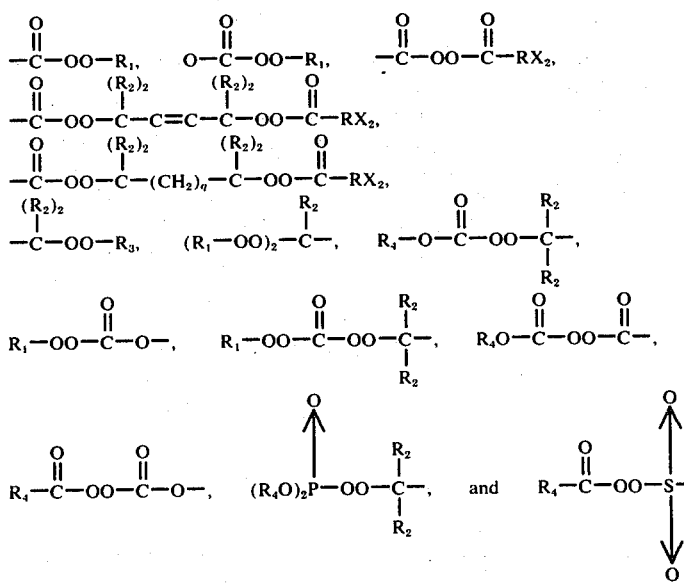

6. $R_1$ is a tertiary alkyl group having 4–8 carbon atoms;
7. $R_2$ is aliphatic radical of 1 to 12 carbons or cycloaliphatic of 3 to 12 carbons.

8. $R_3$ is t-alkyl or aralkyl each having not more than 10 carbon atoms;
9. $R_4$ is aliphatic radical of 1 to 12 carbons; cycloaliphatic radical of 3 to 12 carbons; or aromatic radical of 6 to 12 carbons.

II. A polymer, containing at least one peroxide group, having the formula $$([A_n(-R-D_n)_n]y-P)_w-Z$$

where:
1. A is selected from the class consisting of

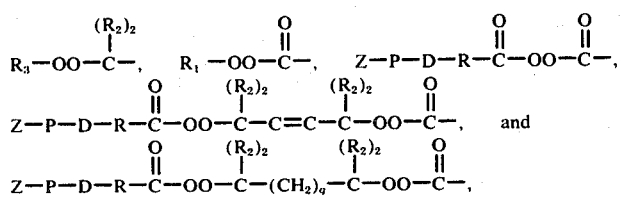

2. (P-)D is selected from the class consisting of

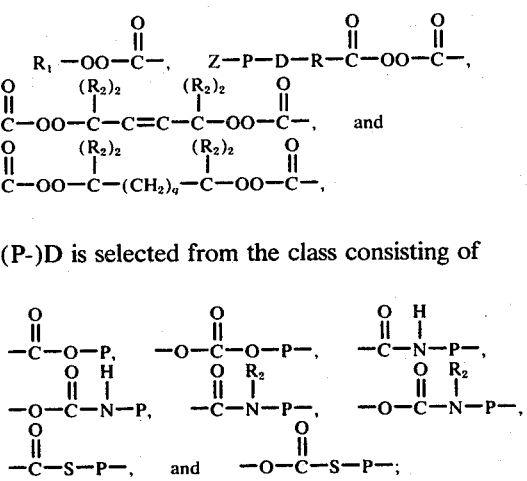

3. P is a $v + 1$ valent polymeric residue;
4. Z is selected from the class consisting of H, OH, $NH_2$, $NHR_2$, SH, and $R_2O-$;
5. $v$ is an integer equal to 1–100;
6. $w$ is an integer equal to 1–100;
7. $n$ is an integer equal to 1–2;
8. R is an aliphatic, cycloaliphatic or aromatic radical having 2–4 valences;
9. $R_1$ is t-alkyl having 4–8 carbon atoms;
10. $R_2$ is aliphatic radical of 1 to 12 carbons or cycloaliphatic of 3 to 12 carbons.

11. $R_3$ is t-alkyl or aralkyl each having not more than 10 carbon atoms; and
12. $q$ is an integer equal to 2–4.

III. The invention includes a method of preparing block and graft polymers by reacting a vinyl-type monomer with polymer II under conditions to decompose the peroxide. Example: A block polymer is prepared by forming a styrene solution, 15 parts by weight, and the polymer product of hydroxyl terminated polybutadiene and bis(4-chloroformylbutyryl) peroxide, 5 parts by weight, and heating said mixture for about 7 hours at 70° C–100° C, under an inert atmosphere.

IV. The invention includes a method of preparing a peroxide having an acylating function by reacting an organic peroxide having at least one reactive group, capable of being converted to an acylating function, selected from the class consisting of carboxyl and hydroxyl, said reactive group being the only group in said peroxide capable of reacting with the acyl function forming reactant; with an acyl function forming reactant selected from the class consisting of $CO(B)_2$, $P(B)_3$, $P(B)_5$, $PO(B)_3$, $SO(B)_2$, $SO_2(B)_2$ where B is selected from the class consisting of Cl and Br; at a temperature between about 0° and 80° C, said maximum temperature being controlled to avoid substantial decomposition of the peroxy groups present in the reaction zone.

V. The invention includes a method for preparing a peroxide having at least one acylating function of the general formula $X_n-R_p-Y'_m$ by peroxidizing a compound having at least two acylating functions, as the only peroxidizable substituents, under conditions to prepare a peroxide product having at least one acylating function, where: I) R, X, $R_1$, $R_2$, $R_3$, $m$, $n$, $p$, and $q$ have the aforesaid definitions and II) Y' is selected from the class consisting of

DESCRIPTION OF THE INVENTION AND EXAMPLES

COMPOUNDS I

In the compound $X_n-R_p-Y_m$, R is aliphatic, cycloaliphatic or aromatic having 2–4 valences available for X and Y. More commonly these are hydrocarbon radicals of these types. Desirably the aliphatic hydrocarbon radical has 1–20 carbon atoms — preferably this is an alkyl radical. Desirably the cycloaliphatic hydrocarbon radical having 4–10 ring carbon atoms — preferably this is a cycloalkyl radical. Desirably the aromatic hydrocarbon radical has one or two benzene rings, which can be condensed as in naphthenylene or joined as in biphenylene.

X is an acylating function which may be acyl chloride or bromide; chloro or bromoformate; or anhydro. Where X is anhydride, R must be a tri or tetravalent radical.

Y is a peroxy containing group, as defined in the summary herein. Some of the defined groups also include an acylating function X, affording a compound having a multiplicity of acylating functions.

"n and m" are integers each equal to 1–2; $n$ and $m$ need not be equal to each other.

$R_1$ is a tertiary alkyl group having 4–8 carbon atoms. This is to be understood as

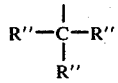

where R'' is alkyl.

$R_2$ is an aliphatic group hving 1–12 carbon atoms or cycloaliphatic group having 3–12 carbon atoms.

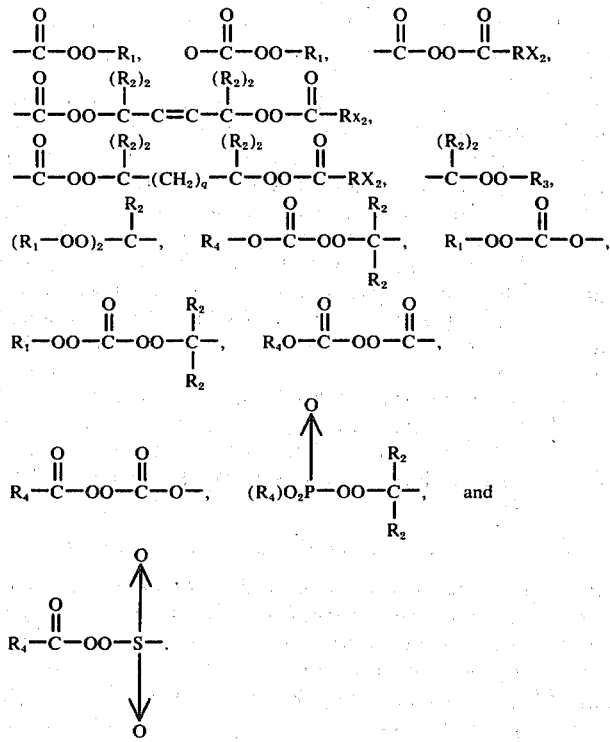

$R_4$ is an aliphatic radical of 1 to 12 carbons, cycloaliphatic radical of 3 to 12 carbons or an aromatic radical of 6 to 12 carbons.

$R_3$ is t-alkyl having not more than 10 carbon atoms or aralkyl, such as cumyl, having not more than 10 carbon atoms.

"$q$" is an integer equal to 2–4.

Three procedures for preparing compounds coming with "Compounds I" are set out in the Examples Section herein.

Compounds A are useful initiators for the polymerization of vinyl-type monomers. Compounds A can be reacted with polymeric materials containing terminal or pendant hydroxyl, amino, and mercapto groups or any other functionality that can be acylated. (Examples I, II, III, IV). Compounds containing two acylating groups can be reacted with difunctional monomers to obtain condensation polymers like: polyesters, polyamides, etc. (Example VI) containing intermittent peroxy groups along the polymer backbone. These peroxy compounds containing acylating groups are useful as intermediate for the preparation of other derivatives and they will undergo any reaction where acid halides, haloformates and anhydrides are normally used.

POLYMERS II

In the polymer $([A_n\text{-}R\text{-}D_n]_v\text{-}P)_w\text{-}Z$ as defined in the summary the remarks made under Compound I in this description with respect to the various "R" radicals are applied to polymer II herein.

"Z" is a terminal or pendant group selected from the group —H, —OH, —$NH_2$, —$NHR_2$, —SH and —OR.

"$q$" is an integer equal to 2–4.

"$n$" is an integer equal to 1–2 and the various "$n$'s" in the polymer formula need not have the same value.

In order to show the attachment of "P" to the "D" group in the polymer, "D" is defined as "(P-)D" as set forth in the II of the summary herein.

"$v$" and "$w$" are integers each equal to 1–100; they may have the same or different values.

P is a $v + 1$ valent polymeric residue such as a polyether, polyester, polyamide, polycarbonate, polybutadiene, polystyrene, poly(vinyl alcohol), partially hydrolyzed poly(vinyl acetate), cellulose, polybutadiene-polystyrene copolymer, and any other polymeric material. More specifically polyether containing aliphatic, cycloaliphatic, aromatic, and heterocyclic diradicals linked to the oxygen atoms; polyester, such as prepared from aliphatic, cycloaliphatic, aromatic, and heterocyclic dibasic acids and dihydroxy compounds; polyamide, such as prepared from aliphatic, cycloaliphatic, aromatic, and heterocyclic dibasic acids and diamines; polycarbonate, such as prepared from aliphatic, cycloaliphatic, aromatic, and heterocyclic dihydroxy compounds and phosgene or aliphatic, cycloaliphatic, aromatic and heterocyclic bis(chloroformates).

"A" is a peroxy containing group as defined in II in the summary.

Polymer II can be prepared by reaction with polymeric materials containing terminal or pendant hydroxyl, amino, and mercapto groups or any other functionality that can be acylated. Preparations are illustrated by Examples I, II, III, and IV. Polymers II can be used to prepare graft and block polymers with vinyl monomers by decomposing the peroxide present in the polymer (Example VII, VIII, IX, XI).

Polymers II can be used in making graft and block polymers. These block and graft copolymers are useful as compatibilizing agents. The great majority of homopolymers are incompatible with each other. However, when block and/or graft copolymers of two incompatible homopolymers are present, the system becomes much more, if not completely, compatibilized (see Examples VIII and IX).

III. METHOD OF PREPARING BLOCK AND GRAFT POLYMERS

These novel peroxy containing polymers II can be used to make block and graft copolymers by treating them with polymerizable vinyl-type monomers under conditions where the peroxy-carbon linkage is decomposed (ruptured) into free radicals at a rate and temperature suitable for polymerizing the vinyl monomer itself. Suitable vinyl-type monomers include: styrene, butadiene, isoprene, acrylonitrile, vinyl chloride, ethyl acrylate, methyl methacrylate, vinyl acetate, acrylic acid, vinyl stearate, vinylidene chloride, and the like.

Any of the conventional procedures for decomposing the peroxide, such as heating to the proper temperature, activation with amines or transition metal salts, and ultra violet irradiation can be used.

Illustrative block and graft polymers are prepared in Examples VII, VIII, IX and XI.

It is known that when two different polymers are brought in solution — really a dispersion because of the low solubility of polymer in the common organic solvents — in a common solvent, over a period of time the solution segregates into two layers, having different polymeric compositions. Apparently homogeneous melts of two different polymers frequently on solidifying show undesired segregation or heterogeneous dispersion of one polymer throughout the continuous phase of the other polymer. Since physical mixtures (dispersion) of two different polymers afford very desirable physical properties, if a homogeneous mass is maintained, stability of the dispersion is of importance. A "third" component of the mix which improves the dispersion stability of the mix is known as a stabilizer — in certain special areas, the stabilizer is referred as a compatibility agent.

The ability to stabilize is tested in the laboratory by empirical tests where the "stabilized" solution is compared to a control solution. The time for the appearance of two distinct layers is measured. It is to be emphasized that the results cannot be used to compare effectiveness in different polymeric systems, since even polymer molecular weight can cause substantial changes in separation time between two systems made from the same monomers. However the laboratory tests are meaningful in terms of screening potential stabilizers.

An important utility of the block and graft polymers made by the method of the invention is as stabilizers (compatibilizers) of solutions of different homopolymers. This utility is demonstrated by Examples VIII and IX.

IV. METHOD OF PREPARING COMPOUND I

It has been discovered that compounds having both at least one peroxy group and at least one acylating function are produced by the acylation of a peroxide having a hydroxyl or carbonyl group. No other group capable of reacting with the acylating agent is present in the peroxide reactant.

The acyl function forming reagent is phosgene ($COCl_2$), $COBr_2$, phosphorus trichloride, phosphorus tribromide, phosphorus pentachloride, phosphorus pentabromide, sulfuryl chloride, sulfuryl bromide, thionyl chloride, or thionyl bromide.

The acylation reaction is carried out at a temperature suitable for the reaction but controlled to avoid substantial decomposition of the peroxy groups present in the reaction zone. The temperature will vary for particular reactant systems but, in general, falls in the range of about 0° to 80° C.

The method IV invention is illustrated by Procedures I, II and III in the Examples herein.

V. METHOD OF PREPARING COMPOUNDS

It has been discovered that compounds having both, at least one peroxy group and at least one acylating function are prepared by peroxidizing a compound having at least two acylating functions, as the only peroxidizable substituents using the agent in an amount such that at least one acylating function is not peroxidized. The class of compounds possible by this method have the general formula $X_n$—$R_p$—$Y'_m$ where X, R, $n$, $m$ and $p$ have the definitions set out in respect to Compound I. Y' includes all the members set out in the definition of Y except for

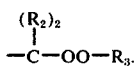

The peroxidizing agent may be a suitable organic hydroperoxide or in some instance an alkali metal peroxide.

EXAMPLES

Compounds of the invention containing an acylating group and a peroxy group were prepared by one of the following procedures:

EXAMPLE OF PROCEDURE I

Preparation of t-butyl o-(chloroformyl)peroxybenzoate

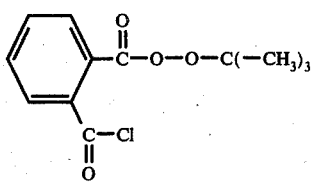

To a suspension of t-butyl o-(carboxy)peroxybenzoate (16.2g. 0.06 moles) in 100 ml. of benzene at +6° to +24° C but preferably at +6° to +10° C was added in a single portion phosphorous pentachloride (12.6g. 0.06 moles).

The mixture was stirred for two hours or longer at +24° to +80° C but preferably at +24° to +40° C.

At the end of the reaction period the mixture was diluted with ice-water and the organic phase separated, washed to neutrality, dried over anhydrous magnesium sulfate, filtered and the solvent evaporated under reduced pressure.

A viscous liquid was obtained (14g.).

Calculated yield for $C_{12}H_{13}ClO_4$ 15.1g. or 92.7% of the theory. S.P.I, at 115° C gave: Gel Time 6.3 min.; Cure Time 7.9; Peak °F 443 Calculated A(O) 6.24%. Found 5.95% or 95.5% pure.

EXAMPLE OF PROCEDURE II

Preparation of 2-(t-butylperoxycarbonyl)ethyl chloroformate

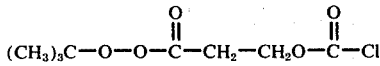

To 75 ml. of pentane at −10° to +5° C was added 39.6g. of phosgene. To this mixture was added a mixture of t-butyl-3-hydroxyperoxypropionate (38g. 0.2 moles of 85% pure products) and pyridine (15.8g. 0.2 moles) in diethyl ether over a period of one hour.

The reaction temperature during the addition was controlled at −10° to +20° C but preferably at 0±1° C.

After the addition was completed the mixture was allowed to stir for 30 minutes while the reaction temperature was allowed to rise to +25° C ± 1° C.

After filtration of the pyridine hydrochloride the mixture was stripped under reduced pressure. The residue was dissolved in diethyl ether and washed with a 10% solution of tartaric acid, 10% solution of sodium bicarbonate and water to neutrality. The ether solution was dried over anhydrous magnesium sulfate, filtered and the solvent evaporated under reduced pressure. A liquid was obtained, (40g.).

Theoretical yield for $C_8H_7ClO_5$ 44.9g. or 89% of the theory. Calculated A(O) 7.15%. Found A(O) 6.84%, calculated % Cl 15.8% found 12.7%.

EXAMPLE OF PROCEDURE III

Preparation of bis(4-chloroformylbutyryl) peroxide

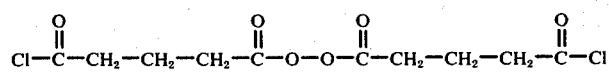

A mixture of glutaric acid peroxide (10.5g. 0.04 moles) and thionyl chloride (30 ml.) at 0° to +30° C preferably at +10° to +24° C was treated with one drop or more of pyridine. The mixture was allowed to react for 24 hours or longer at +30° to +80° C but preferably at +30° C to +40° C. After this time the mixture was evaporated under reduced pressure.

A viscous liquid was obtained, (9g.).

Calculated yield for $C_{10}H_{12}Cl_2O_6$ 11.9g. or 75.6% of the theory.

Calculated A(O) 6.35%, found A(O) 5.11%. Calculated %Cl 23.9 found Cl 25.2%.

Compounds prepared by one of these procedures are tabulated in Table I.

TABLE I

| Names & Structure | Chlorinating agent | % Yield uncorr. | Purity | Theor. (O) | Found (O) | Theor. Cl% | Found Cl% |
|---|---|---|---|---|---|---|---|
| (CH₃)₃—C—O—C(=O)—C(=O)—CH₂—CH₂—C(=O)—C(=O)—Cl<br>2-(t-butylperoxycarbonyl)-ethyl chloroformate | COCl₂ | 89.0 | 95.6 | 7.15 | 6.84 | 15.8 | 12.7 |
| [benzene ring with ortho C(=O)—O—O—C(CH₃)₃ and C(=O)—Cl]<br>t-butyl o-(chloroformyl)peroxy-benzoate | PCl₅ | 92.7 | 95.5 | 6.24 | 5.95 | — | — |
| [benzene ring 1,2,4,5-tetrasubstituted with Cl—C(=O)—, (CH₃)₃CO—O—C(=O)—, —C(=O)—OCC(CH₃)₃, —C(=O)—Cl]<br>-t-butyl 2,5-di(chloroformyl) di-peroxy-terphthalate | PCl₅ | — | 62 | 7.35 | 4.5 | 16.3 | 10.1 |
| CH₃—C(O—O—C(CH₃)₃)(O—O—C(CH₃)₃)—CH₂—CH₂—O—C(=O)—Cl<br>3,5-11(t-butylperoxy)butyl chloroformate | COCl₂ | — | — | 10.2 | 10.14 | 11.2 | 10.6 |
| [cyclohexane with S, substituents C(=O)—OC(CH₃)₃ and C(=O)—Cl]<br>t-butyl-2-(chloroformyl)-hexahydroperoxybenzoate | SOCl₂ | 99.8 | 100 | 6.2 | 6.2 | — | — |
| (CH₃)₃—C—O—OC(=O)—CH=CH—C(=O)—Cl<br>3-(t-butylperoxycarbonyl)-aeryloyl chloride | PCl₅ | 50 | 54.8 | 7.75 | 4.23 | — | — |
| (CH₃)₃C—OC(=O)—CH₂—CH₂—C(=O)—Cl<br>3-(t-butylperoxycarbonyl)-propionyl chloride | PCl₅ | — | 98.5 | 7.7 | 7.59 | — | — |
| (Cl—C(=O)—CH₂—CH₂—CH₂—C(=O)—O)₂<br>bis(4-chloroformylbutyryl) peroxide | SOCl₂ | — | 95.5 | 5.35 | 5.11 | 23.9 | 25.2 |
| CH₃—C(CH₃)(O—O—C(CH₃)₃)—CH₂—CH(CH₃)—O—C(=O)—Cl<br>1,3-dimethyl-3-(t-butylperoxy)butyl chloroformate | COCl₂ | — | — | — | — | 14.01 | 11.7 |

| | Chlorinating Agent | Yield Uncorr. | Purity | Theor. Cl% | Found Cl% |
|---|---|---|---|---|---|
| 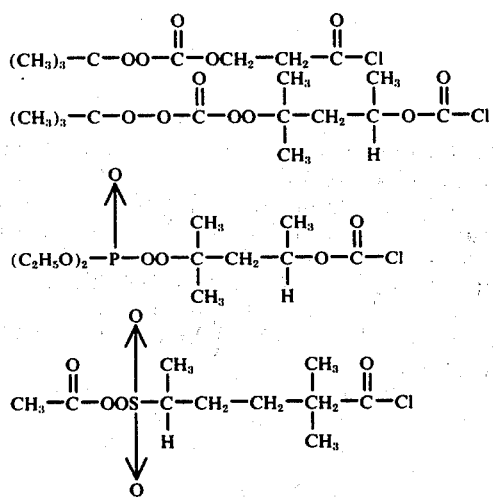 1,3-dimethyl-3-(n-butoxycarbonylperoxy)butyl chloroformate | COCl$_2$ | 84 | 94.2 | 11.75 | 11.2 |

Other compounds that can be prepared by conventional methods are:

$$(CH_3)_3-C-OO-\underset{\underset{O}{\|}}{C}-OCH_2-CH_2-\underset{\underset{O}{\|}}{C}-Cl$$

$$(CH_3)_3-C-O-O-\underset{\underset{O}{\|}}{C}-OO-\underset{\underset{CH_3}{\overset{CH_3}{|}}}{C}-CH_2-\underset{\underset{H}{\overset{CH_3}{|}}}{C}-O-\underset{\underset{O}{\|}}{C}-Cl$$

$$(C_2H_5O)_2-\overset{\overset{O}{\uparrow}}{P}-OO-\underset{\underset{CH_3}{\overset{CH_3}{|}}}{C}-CH_2-\underset{\underset{H}{\overset{CH_3}{|}}}{C}-O-\underset{\underset{O}{\|}}{C}-Cl$$

$$CH_3-\underset{\underset{O}{\|}}{C}-OO\overset{\overset{O}{\uparrow}}{\underset{\underset{O}{\downarrow}}{S}}-\underset{\underset{H}{\overset{CH_3}{|}}}{C}-CH_2-CH_2-\underset{\underset{CH_3}{\overset{CH_3}{|}}}{C}H_2-\underset{\underset{O}{\|}}{C}-Cl$$

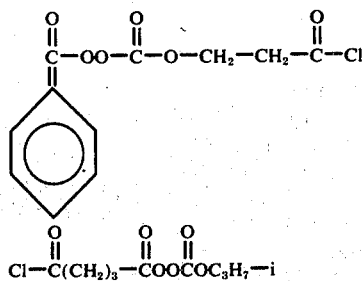

Polymers of the invention and the utility of certain compounds of the invention is illustrated by the following working examples:

EXAMPLE I

Reaction of cellulose with 2-(t-butylperoxycarbonyl)ethyl chloroformate 2.5g. of cellulose powder (Fisher filtration accelerator NO 9-906) was treated with 20 ml. of sodium hydroxide (50%) and allowed to stand overnight.

The following day the mixture was filtered and the solid suspended in water and reacted with 4g. of 2-(t-butylperoxycarbonyl) ethyl chloroformate and allowed to stir for 24 hours at +40° C to +100° C but preferably +40° C to +50° C. After this time the mixture was filtered and the solid washed with benzene and diethyl ether and air dried.

A solid (5g.) was obtained containing 0.12% A(O).

SPI exotherm in polyester resin at 115° C and 1% concentration gave the following:

| Gel Time in minutes | 7.2 |
|---|---|
| Cure Time in minutes | 11.9 |
| Peak in ° F | 313° |

EXAMPLE II

Reaction of hydroxyl-terminated polybutadiene with 2-(t-butylperoxycarbonyl)ethyl chloroformate

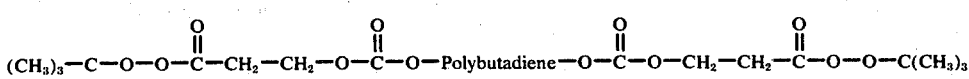

To a mixture of 17.6g. of hydroxyl-terminated polybutadiene liquid resin (Sinclair R-15 M resin equivalent weight - 1330, containing 0.75 meq. OH per gram), diethyl ether and triethylamine (1.4g .0132 moles) was added a solution of 2-(t-butylperoxycarbonyl)-ethyl chloroformate (3.8g. of 90% product, 0.0132 moles) in diethyl ether. The mixture was reacted for 4 hours at +20° C to +100° C but preferably at +20° to +40° C.

After filtration of the triethylamine hydrochloride and evaporation of the solvent a viscous liquid was obtained (14g.) that contained 0.91% A(O).

SPI exotherm in polyester resin at 115° C and 2% concentration gave the following:

| Gel Time in Minutes | 5.4 |
|---|---|
| Cure Time in Minutes | 7.5 |
| Peak in ° F | 428° |

EXAMPLE III

Reaction of hydroxyl terminated polybutadiene with t-butyl o(chloroformyl)peroxybenzoate

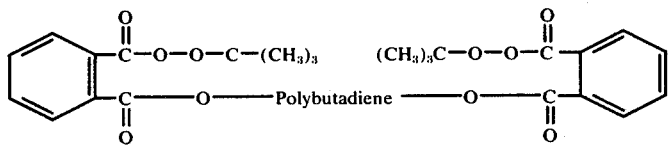

To a solution of 17.6g. of a hydroxyl-terminated polybutadiene liquid resin (equivalent weight 1330g. containing 0.75 meq/g) and triethylamine (1.4g. 0.0132 moles) in diethyl ether was added a solution of t-butyl o-(chloroformyl)peroxybenzoate (0.0132 moles) in benzene.

After filtration of the triethylamine hydrochloride and evaporation of the solvent a viscous liquid was obtained (16g.) that contained 0.27% A(O).

SPI exotherm in polyester resin at 115° C and 2% concentration gave the following:

| | |
|---|---|
| Gel Time in minutes | 15.1 |
| Cure Time in minutes | 22.0 |
| Peak in ° F | 332° |

EXAMPLE IV

Preparation of polyether containing an acylperoxy group $$\left[ CH_3O(CH_2-CH_2O)_n-\overset{O}{\underset{\|}{C}}-CH_2-CH_2-CH_2-\overset{O}{\underset{\|}{C}}-O \right]_2$$

To a solution of 15g. (0.02 moles) of a monohydroxyl-terminated polyether (Union Carbide Carbowax-750, molecular weight 715–785) and 2.02g. (0.02 moles) triethylamine in diethyl ether was added a solution of 3.2g. (0.01 moles) bis[4-(chloroformyl)butyryl] peroxide in benzene.

The mixture was allowed to stir for six hours.

After filtration of the triethylamine hydrochloride, the ether solution was evaporated under reduced pressure.

A viscous liquid was obtained (16g.) containing 0.54% A(O).

$n$ is 15–17 in the product formula.

EXAMPLE V

Reaction of hydroxyl-terminated polybutadiene with bis(4-chloroformylbutyryl) peroxide in presence of ethanol.

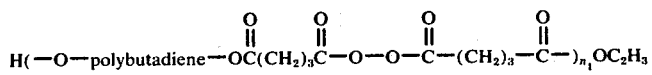

To a solution of 35.2g. of hydroxyl-terminated polybutadiene (Sinclair R-15 M resin) and 2g. (0.0264 moles) of triethylamine in diethyl ether was added a solution of bis(4-chloroformylbutyryl) peroxide (96.7%) (4.7g. 0.0132 moles) in diethyl ether.

After the addition was completed, absolute ethanol was added (1.2g. 0.0264 moles). The mixture was reacted for two hours. After filtration of the triethylamine hydrochloride, the ether solution was evaporated under reduced pressure. A viscous liquid was obtained (37g.) containing 0.30% A(O).

$n_1$ is greater than 1 in the product formula.

EXAMPLE VI

Preparation of polyester containing peroxide

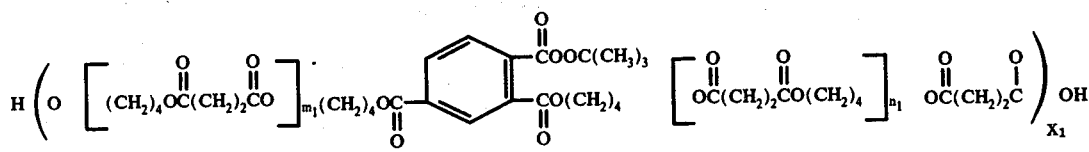

To 2.7g. (0.03 moles) of 1,4-butanediol and 7.5g. (0.075 moles) of triethylamine dissolved in diethyl ether was added a solution of 1.9g. (0.005 moles) t-butyl 2,4(5)-(dichloroformyl)peroxybenzoate and 3.9g. (0.025 moles) of succinoyl dichloride in benzene.

After filtration of the triethylamine hydrochloride, the organic phase was stripped under vacuum. A viscous residue was obtained. SPI exotherm in polyester resin at 115° C and 1% concentration gave the following:

| | |
|---|---|
| Gel Time in minutes | 4.1 |
| Cure Time in minutes | 6.5 |
| Peak in ° F | 385° |

"$m_1$, $n_1$, and $X_1$" are each equal to more than 1 in the general formula shown for the polyester product.

EXAMPLE VII

Preparation of block copolymer with styrene from product prepared in Example I

Cellulose(polystyrene)$_{n_1}$

To 15 ml. of styrene placed in a tube was added 0.5g. of the product prepared in Example I. The tube was sealed under an atmosphere of nitrogen and heated for six hours at +60° C to +100° C.

The reaction product was then extracted with chloroform for 24 hours then dried under vacuum at 50° C for six hours.

The block copolymer formation was confirmed by pyrolysis analysis with Vapor Phase Chromatography (Perkin-Elmer 154 model). The cellulose containing peroxide (Example I) was pyrolyzed and the gases passed through a 6 ft. column od diisodecyl phthalate ($10^3$ low 4X). The chromatogram showed peaks at 1.75; 1.85; 1.95; and 2.25 minutes.

Similarly polystyrene was pyrolyzed. The chromatogram showed peaks at 1.8; 3.4; 4.7; and a major peak between at 9.3 and 10.3 minutes.

The prepared block copolymer was also pyrolyzed.

From the peaks obtained in this chromatogram (1.75; 1.85; 1.95; 2.25; 3.4 and a peak between 9.3 and 9.73 minutes) one concludes that the block copolymer contained cellulose and styrene.

In order to assure that the chloroform extraction was satisfactory, polystyrene was polymerized in presence of cellulose with AIBN azo-bis(isobutyrylnitrile). The polymer obtained, after extraction with chloroform for 24 hours, was pyrolyzed and analyzed by Vapor Phase Chromatography. No polystyrene peaks could be observed in this polymeric material after the extraction indicating that the extraction technique was satisfactory.

EXAMPLE VIII

Preparation of block copolymer with styrene from product obtained in Example IV.

Polyether-Polystyrene

To 15g. of styrene placed in a tube is added 5g. of the product obtained on Example IV. The tube is sealed under a nitrogen atmosphere and heated for seven hours at +10° to +100° C. The polymer obtained from the reaction is dissolved in benzene and precipitated with odorless mineral spirit. The formation of the block copolymer is demonstrated by the "demixing test" similar to those of Hughes and Brown (4) and Molau (5): (4) L. J. Hughes and G. L. Brown, J. Appl. Polymer Sci. 7-59 (1963); (5) G. E. Molau, J. Polymer Sci A3-1267 (1965). The control is a 50/50 mixture of 40% polystyrene and 40% solution of a monohydroxyl terminated polyether (Carbowax-750) in chloroform solution. After these were well mixed the demixing time was 30 minutes. A 40% solution of the block prepared in chloroform showed no demixing in 22.5 hours.

A mixture of 1:1:1 of 40% solutions of polystyrene, Carbowax-750 and the prepared block in chloroform after they were well mixed showed a demixing time of 90 minutes.

EXAMPLE IX

Preparation of block copolymers with styrene from product obtained in Example V.

Polystyrene-Polybutadiene

To 15g. of styrene placed in a tube is added 5g. of the product obtained on Example V. The tube is sealed under a nitrogen atmosphere and heated for 7 hours at +70° C to +100° C. The polymer obtained from the reaction is dissolved in benzene and precipitated with odorless mineral spirit. The polymer is dried in a vacuum oven for sixteen hours at +50° C and tested by the demixing test. (4)–(5).

The control is a 50/50 mixture of 15% polystyrene and 15% hydroxyl terminated polybutadiene in benzene solution. After these are well mixed, a demixing time of twenty minutes was obtained. A 15% solution of the block copolymer showed no demixing in 13 days. A mixture of 1:1:1 of 15% solutions of polystyrene, hydroxyl terminated polybutadiene and the block copolymer in benzene gave a demixing time of 6 hours.

EXAMPLE X

Reaction of hydroxy-terminated polybutadiene-styrene with t-butyl o-(chloroformyl)peroxybenzoate $$\underset{O}{\underset{\|}{\text{C}}}\text{—O—O—C—(CH}_3)_3 \qquad (\text{CH}_3)_3\text{C—O—O—}\underset{O}{\underset{\|}{\text{C}}}$$
$$\underset{O}{\underset{\|}{\text{C}}}\text{—O—Polybutadiene—Polystyrene—copolymer—O—}\underset{O}{\underset{\|}{\text{C}}}$$

To a solution of 17.6g. of hydroxyl-terminated polybutadiene polystyrene copolymer (Sinclair C-S-15 resin, equivalent weight 1330) containing 0.75 meq/gm) and triethylamine (1.4g. 0.0132 moles) in diethyl ether was added a solution of t-butyl o-(chloroformyl) peroxybenzoate (0.0132 moles) in benzene.

After filtration of the triethylamine hydrochloride and evaporation of the solvent a viscous liquid was obtained (16g.) that contained 0.43 A(O).

EXAMPLE XI

Preparation of block copolymer with acrylonitrile from the copolymer containing peroxide in Example X.

Polybutadiene-Polystyrene-Polyacrylonitrile

Into a tube was placed 5g. of the copolymer containing peroxide (Example X) and 60g. of toluene which is not a solvent for polyacrylonitrile.

The mixture was cooled at 0° C and 25g. of acrylonitrile was added. The tube was sealed under nitrogen and it was heated at 100° C for 27 hours.

A blank was prepared containing 0.5g. of polybutadiene-polystyrene copolymer (Sinclair C-S-15), 2.5g. acrylonitrile and 6g. of toluene and it was heated at 100° C for 27 hours.

After this time the two solutions were cooled down to 23°–25° C and centrifugated for 4 hours. The blank failed to give any solid while the other sample separated 7g. of polyacrylonitrile.

The toluene solution after separation of the solid was precipitated with methanol and 12g. of solid was obtained. The increase weight of the soluble polymer was a proof of the block formation.
We claim:
1. A peroxide having the formula
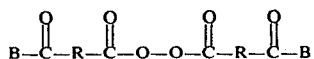
where:
1. R is hydrocarbon aliphatic of 1–20 carbons, cycloalkyl of 4–10 carbons or hydrocarbon aromatic of 6–12 carbons; and
2. B is Cl— or Br—.
2. The compound of claim 1 where R is aliphatic hydrocarbon having 1–20 carbon atoms.
* * * * *